US00PP18045P2

(12) United States Plant Patent
Schräder

(10) Patent No.: US PP18,045 P2
(45) Date of Patent: Sep. 18, 2007

(54) ***LOBELIA* PLANT NAMED 'GRÜLO 06'**

(50) Latin Name: *Lobelia richardii*
Varietal Denomination: Grülo 06

(75) Inventor: Ralf Schräder, Lüdinghausen (DE)

(73) Assignee: Grunewald Veredlings B.V., Bocholt (DE)

( * ) Notice: Subject to any disclaimer, the term of this patent is extended or adjusted under 35 U.S.C. 154(b) by 16 days.

(21) Appl. No.: 11/188,976

(22) Filed: Jul. 25, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

UPOV–ROM GTITM, Plant Variety Database, 2006/02, GTI Jouve Retrieval Software, citation for 'Grulo 06'.*

* cited by examiner

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Lobelia* plant named 'Grülo 06', characterized by its upright, outwardly spreading to cascading plant habit; freely branching habit; early and freely flowering habit; and blue and white bi-colored flowers.

1 Drawing Sheet

Botanical designation: *Lobelia richardii.*
Cultivar denomination: 'Grülo 06'.

BACKGROUND OF THE INVENTION

The present Invention relates to a new and distinct cultivar of *Lobelia* plant, botanically known as *Lobelia richardii,* and hereinafter referred to by the name 'Grülo 06'.

The new *Lobelia* is a product of a planned breeding program conducted by the Inventor in 's-Gravenzande, The Netherlands. The objective of the breeding program was to develop new *Lobelia* cultivars with a cascading habit, larger flowers and attractive flower colors.

The new *Lobelia* originated from a cross-pollination made by the Inventor in May, 2002 of a proprietary selection of *Lobelia richardii* identified as code number IO 8, not patented, as the female, or seed, parent with a proprietary selection of *Lobelia richardii* identified as code number IO 11, not patented, as the male, or pollen, parent. The new *Lobelia* was discovered and selected by the Inventor from within the resultant progeny from the above-mentioned cross-pollination in a controlled environment in 's-Gravenzande, The Netherlands in August, 2002.

Asexual reproduction since September, 2002 of the new cultivar by terminal cuttings in a controlled environment in 's-Gravenzande, The Netherlands, has shown that the unique features of this new *Lobelia* are stable and reproduced true to type in successive generations.

SUMMARY OF THE INVENTION

The following traits have been repeatedly observed and are determined to be the unique characteristics of 'Grülo 06'. These characteristics in combination distinguish 'Grülo 06' as a new and distinct cultivar:

1. Upright, outwardly spreading to cascading plant habit.
2. Freely branching habit.

3. Early and freely flowering habit.
4. Blue and white bi-colored flowers.

Plants of the new *Lobelia* and the female parent selection differ primarily in flower size as plants of the new *Lobelia* have larger flowers than plants of the female parent selection. Plants of the new *Lobelia* and the male parent selection differ primarily in plant form as plants of the male parent selection are longer and have a more trailing plant habit.

Plants of the cultivar Grülo 06 can be compared to the cultivar Weslobigblue, disclosed in U.S. Plant Pat. No. 12,634. However, in side-by-side comparisons conducted in 's-Gravenzande, The Netherlands, plants of the new *Lobelia* and the cultivar Weslobigblue differed in the following characteristics:

1. Plants of the new *Lobelia* were taller than plants of the cultivar Weslobigblue.
2. Plants of the new *Lobelia* flowered about two weeks earlier than plants of the cultivar Weslobigblue.
3. Plants of the new *Lobelia* had slightly smaller flowers than plants of the cultivar Weslobigblue.
4. Flowers of plants of the new *Lobelia* were darker blue in color than flowers of plants of the cultivar Weslobigblue.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description, which accurately describe the actual colors of the new *Lobelia.* The photograph comprises a side view of a typical plant of 'Grülo 06' grown in a container.

DETAILED BOTANICAL DESCRIPTION

Plants of the cultivar Grülo 06 have not been observed under all possible environmental conditions. The phenotype may vary somewhat with variations in environment such as temperature and light intensity without, however, any variance in genotype.

In the following description, color references are made to The Royal Horticultural Society Colour Chart, 2001 Edition, except where general terms of ordinary dictionary significance are used. Plants used for the aforementioned photograph and following description were grown in an outdoor nursery under conditions that closely approximate commercial production conditions during the spring and summer in 's-Gravenzande, The Netherlands. During the production of the plants, day temperatures ranged from 16° C. to 24° C., night temperatures ranged from 8° C. to 14° C. and light levels ranged from 20,000 to 45,000 lux. Plants were pinched once during the production period. Plants were about four months from planting when the photographs and description were taken.

Botanical classification: *Lobelia richardii* cultivar Grülo 06.

Parentage:

*Female parent.*—Proprietary selection of *Lobelia richardii* identified as code number IO 8, not patented.

*Male parent.*—Proprietary selection of *Lobelia richardii* identified as code number IO 11, not patented.

Propagation:

*Type cutting.*—Terminal vegetative cuttings.

*Time to initiate roots.*—About 8 to 10 days at 16° C.

*Time to develop roots.*—About three to four weeks at 16° C.

*Root description.*—Fine, fibrous and well-branched; color, 162C.

Plant description:

*Plant form/habit.*—Upright and outwardly spreading to cascading plant habit; plants eventually become spherical in form. Plants uniform and freely branching with lateral branches potentially forming at every node; dense and bushy plant habit; pinching plants enhances branching. Vigorous growth habit.

*Plant height.*—About 30 cm.

*Plant length* (*soil level to lateral branches apices*).—About 30 to 40 cm.

*Plant diameter.*—About 25 to 30 cm.

*Lateral branch description.*—Quantity of primary lateral branches: About 15.

*Length.*—About 25 to 30 cm. Diameter: About 1 to 1.5 mm. Internode length: About 2 to 3 cm. Texture: Smooth, glabrous. Color: 146A.

*Foliage description.*—Arrangement: Alternate; simple. Basal leaves: Length: About 3.5 to 4 cm. Width: About 2 to 2.4 cm. Shape: Elliptic to oval. Apex: Rounded. Base: Acute. Margin: Lobed, crenate. Mid-plant and apical leaves: Length: About 3.5 to 4 cm. Width: About 1.6 to 1.8 cm. Shape: Lanceolate. Apex: Rounded. Base: Acute. Margin: Lobed, crenate. Texture, all leaves, upper and lower surfaces: Smooth, glabrous. Venation, all leaves: Pinnate. Color, all leaves: Developing foliage, upper surface: 144A. Developing foliage, lower surface: 143C. Fully developed foliage, upper surface: 146A; venation, 146A. Fully developed foliage, lower surface: 146B; venation, 146A. Petiole length: About 8 to 10 mm. Petiole diameter: About 2 mm. Petiole texture, upper and lower surfaces: Smooth, glabrous. Petiole color, upper and lower surfaces: 146C.

Flower description:

*Flower type and habit.*—Flowers arranged singly at lateral apices. Flowers held mostly outwardly. Flowers not persistent. Older flowers are overgrown by new flowers and foliage. Early flowering; plants begin flower about ten weeks after planting. Freely flowering, about 120 to 150 flowers and flower buds per plant. Flowers not fragrant.

*Flower shape.*—Tubular with three larger lower petals and two upright petals.

*Natural flowering season.*—From early spring until the autumn in The Netherlands.

*Flower longevity on the plant.*—Typically eight to ten days.

*Flower size.*—Diameter: About 1.5 to 1.8 cm. Depth (height): About 1.3 cm.

*Flower buds.*—Length: About 1 to 1.2 cm. Diameter: About 2 to 4 mm. Shape: Oblong. Color: 154D.

*Petals.*—Arrangement: Single whorl of five petals, fused; three larger lower petals and two smaller upper petals. Three lower petals: Length, above throat: About 1.5 to 1.6 cm. Width: About 7 mm. Two upper petals: Length, above throat: About 6 to 8 mm. Width: About 1 to 2 mm. Upper and lower petals: Shape: Obovate. Apex: Rounded. Margin: Entire. Texture, upper and lower surfaces: Smooth, glabrous. Color: When opening, upper surface: 99A; center, N155A. When opening, lower surface: 99B; tube, N155A. Fully opened, lower surface: 99B to 99C; center, N155A. Tube color: Close to 155D. Throat color: Close to 155A. Petal, fully opened, lower surface: 97A to 97B; tube, N144A.

*Sepals.*—Arrangement: Single whorl of five sepals, star-shaped calyx. Length: About 8 to 10 mm. Width: About 1 mm. Shape: Lanceolate. Apex: Acute. Base: Truncate. Margin: Entire. Texture, upper and lower surfaces: Smooth, glabrous. Color, immature, upper and lower surfaces: 144A. Color, mature, upper and lower surfaces: 146A.

*Peduncles.*—Length: About 2 to 2.5 cm. Diameter: About 0.5 to 1 mm. Angle: About 45° from vertical. Strength: Strong. Texture: Smooth, glabrous. Color: 137A.

*Reproductive organs.*—Stamens: Quantity per flower: About five. Anther length: About 2 mm. Anther color: N200C. Filament length: About 1 mm. Pollen amount: Moderate. Pollen color: 3B. Pistils: Quantity per flower: One. Pistil length: About 8 mm. Stigma shape: Rounded. Stigma color: N200B. Style length: About 1 mm. Style color: N200B. Ovary color: N200B. Seeds: Length: About 0.5 mm. Diameter: About 0.5 mm. Shape: Spherical. Color: 200D.

Disease/pest resistance: Plants of the new *Lobelia* have not been noted to be resistant to pathogens and pests common to *Lobelia*.

Temperature tolerance: Plants of the new *Lobelia* have been observed to tolerate temperatures ranging from 0° C. to 40° C.

It is claimed:

1. A new and distinct cultivar of *Lobelia* plant named 'Grülo 06', as illustrated and described.

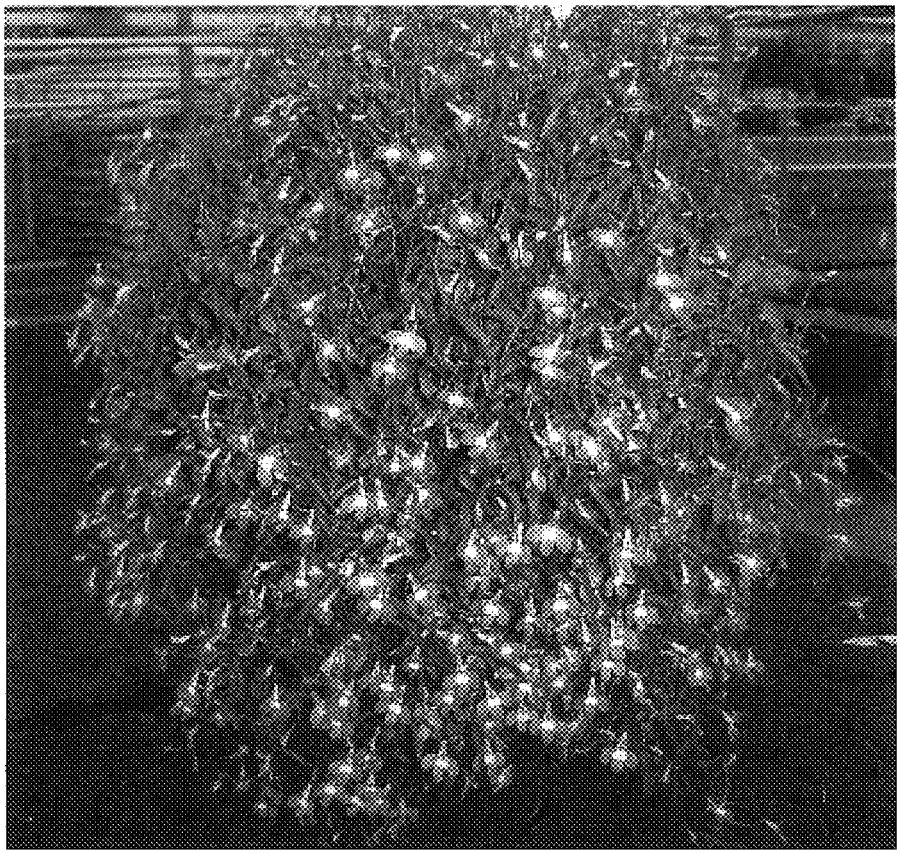

* * * * *